United States Patent [19]

Dunham et al.

[11] Patent Number: 4,879,546
[45] Date of Patent: Nov. 7, 1989

[54] ULTRASONIC HAND-HELD REFRIGERANT LEAK DETECTOR

[75] Inventors: Byron J. Dunham, Sherwood; Gary P. Murray, Montpelier; Don A. Bulla, Bryan, all of Ohio

[73] Assignee: Kent-Moore Corporation, Warren, Mich.

[21] Appl. No.: 344,422

[22] Filed: Apr. 26, 1989

Related U.S. Application Data

[63] Continuation of Ser. No. 126,936, Nov. 30, 1987, abandoned.

[51] Int. Cl.$^4$ ............................................. G08B 17/10
[52] U.S. Cl. ...................................... 340/632; 73/24; 73/40.5 A; 324/58.5 A; 340/693
[58] Field of Search ............................ 340/632–634, 340/627, 693; 324/455, 469, 58.5 A; 73/24, 40.7, 40.5 A; 250/336.1, 343, 373

[56] References Cited

U.S. PATENT DOCUMENTS

| | | | |
|---|---|---|---|
| 3,742,475 | 6/1973 | Lieberman | 340/632 |
| 3,953,844 | 4/1976 | Barr et al. | 340/627 |
| 4,083,231 | 4/1978 | Mennenga | 73/40.7 |
| 4,119,950 | 10/1978 | Redding | 340/632 |
| 4,280,183 | 7/1981 | Santi | 73/24 |
| 4,282,521 | 8/1981 | Liebermann | 340/632 |
| 4,413,503 | 11/1983 | Olivieri | 73/40.7 |
| 4,488,118 | 12/1984 | Jeffers et al. | 340/632 |
| 4,555,932 | 12/1985 | Crosby, Jr. | 73/24 |
| 4,609,875 | 9/1986 | Jeffers | 324/455 |
| 4,630,482 | 12/1986 | Traina | 73/24 |
| 4,662,212 | 5/1987 | Noguchi et al. | 73/24 |
| 4,761,639 | 8/1988 | Pyke et al. | 340/634 |
| 4,831,332 | 5/1989 | Rudisill et al. | 340/632 |

OTHER PUBLICATIONS

Walton, "The Ultrasonic Gas Analyser", (1952).
Haswell et al., "Development of the Sonic Gas Analyser".
"Grubb Parsons, The Sonic Gas Analyser", (1960).
"Grubb Parsons, Sonic Gas Analyser, Type CH", (1961).

*Primary Examiner*—Joseph A. Orsino
*Assistant Examiner*—Jill D. Jackson
*Attorney, Agent, or Firm*—Barnes, Kisselle, Raisch, Choate, Whittemore & Hulbert

[57] ABSTRACT

Hand-held apparatus for detecting presence of halogen refrigerant agents in air in which a pair of ultrasonic transducers are spaced from each other within a measurement probe and test air is continuously drawn between the transducers by a fan. One transducer is energized at constant ultrasonic frequency, and the other transducer is coupled to a rectifier or a phase detector for providing a measurement signal as a function of radiation received at and reflected by such other transducer. A reference signal level is established by selectively sampling and electronically storing of the measurement signal, such that the reference level is automatically or manually updated to reflect changes in ambient conditions. An audio/visual alarm is activated when the measurement signal departs from the ambient reference level by more than a preselected threshold.

22 Claims, 5 Drawing Sheets

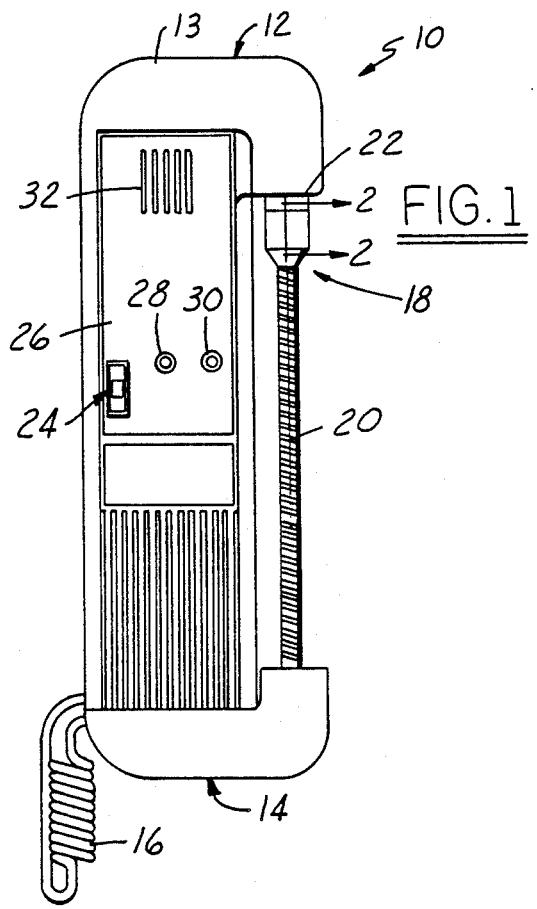
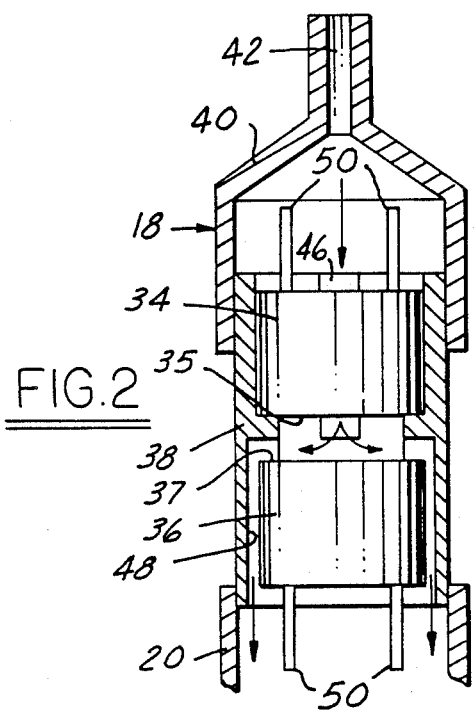
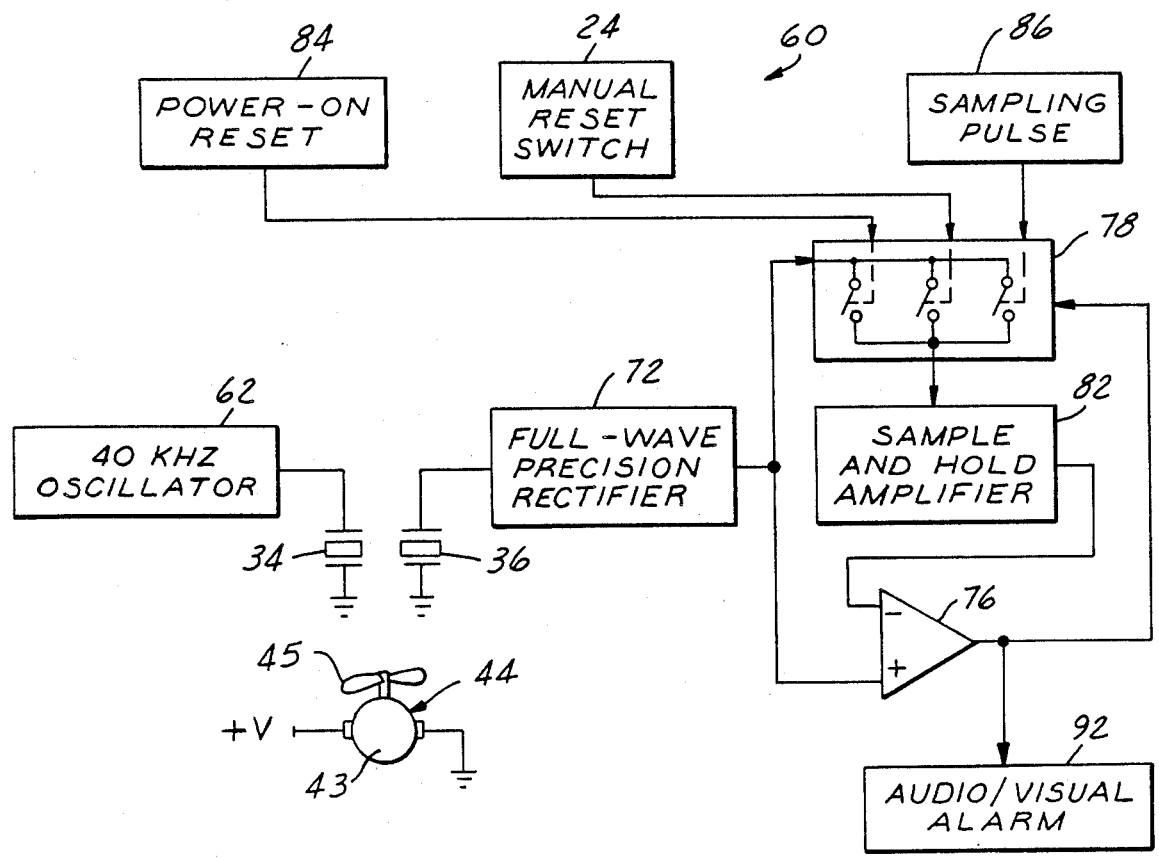

ULTRASONIC HAND-HELD REFRIGERANT LEAK DETECTOR

This is a continuation of co-pending application Ser. No. 07/126,936 filed on Nov. 30, 1987.

The present invention is directed to apparatus for detecting presence of contaminants in air, and more particularly to hand-held apparatus of the described character for detecting and locating a halogen leak in a refrigeration system.

BACKGROUND AND OBJECTS OF THE INVENTION

Walton, "The Ultrasonic Gas Analyser" (1952) discloses a gas analyzer in which a pair of ultrasonic transducers are placed at opposed ends of an elongated sample tube which is "many wavelengths" long. The transmitting transducer is coupled to an oscillator, and the receiving transducer is coupled to a phasemeter which receives a reference input from the oscillator. The phasemeter provides a continuous indication of velocity of radiation in the tube, which in turn varies with impurity concentration. However, the apparatus is subject to inaccuracy due to variations in gas temperature, which also affects radiation velocity. In order to overcome this problem, apparatus is proposed in which a second tube containing a "standard gas" is connected between the oscillator and phasemeter to provide a reference which compensates for temperature variations in both tubes. Hasewell, et al. "Development of the Sonic Gas Analyzer" describes a two-tube instrument of this character marketed by Grubb Parsens in about 1961.

Although instruments of the above-described character can be employed to advantage in a laboratory, the size and complexity of such instruments are not well suited to field use. In applications for detection of refrigerant leaks as in a building air-conditioning system, for example, it would be difficult to manipulate the box containing the two tubes into relatively inaccessible areas in which the refrigerant lines are normally run. Furthermore, the volumes of gas in the sample and reference tubes greatly reduces response time. High voltage corona discharge detectors of the type disclosed is U.S. Pat. Nos. 3,742,475 and 4,488,118 can be more readily manipulated into relatively inaccessible areas, but suffer from other drawbacks.

A general object of the present invention is to provide a device of the described character which is inexpensive to manufacture and reliable in long-term operation, which is contoured and constructed to be held in the hand of an operator and readily manipulated by the operator for locating refrigerant leaks in confined areas, which exhibits reduced battery power consumption, which provides both audible and visible indication of detected contaminant conditions, which automatically accommodates gradual variations in background or ambient contaminant level, and which eliminates any requirement for high voltage at the probe as in corona discharge apparatus of the prior art.

SUMMARY OF THE INVENTION

Apparatus in accordance with the present invention includes a sensor head having a spaced pair of ultrasonic transducers and facility for continuously drawing test air between the transducers. One of the transducers is driven by a constant frequency oscillator, and the output of the other transducer is monitored to provide a measurement signal. The measurement signal is compared to a reference, and contaminant condition of the test air sample is indicated as a function of the measurement signal. The receiving transducer output is monitored for phase angle and amplitude variations in two embodiments of the invention. In accordance with an important feature of the invention, the reference signal is generated by selectively sampling and storing the measurement signal. Thus, the apparatus of the invention effectively monitors for variations in the measurement signal rather than absolute levels thereof. The reference tube of the prior art is completely eliminated. Most preferably, the measurement signal is sampled and stored as the reference signal at preselected periodic intervals, such that gradual changes in contaminant concentration are ignored.

In the preferred embodiment of the invention, the apparatus electronics are contained within a battery-operated enclosure contoured to be held in an operator's hand, with a power/reset switch being positioned on the enclosure for easy manipulation. The sensor head includes a hollow base removably fastened to the enclosure. A probe contains the transducers and is coupled to the base by a hollow flexible conduit. A fan is positioned in the base and draws test air into the probe between the transducers, through the conduit and then out of the base. The fan and transducers in the sensor head are connected to the electronics enclosure by a multiple-conductor coiled cord. The opposed radiating surfaces of the transducers are between 1.0 and 1.5 wavelengths apart. Thus, the size and weight of the probe structure is greatly reduced as compared with the two-tube structures of the art. Furthermore, the probe tip may be readily manipulated with one hand, while the housing reset button can be held in the other for usual observation and operation.

BRIEF DESCRIPTION OF THE DRAWINGS

The invention, together with additional objects, features and advantages thereof, will be best understood from the following description, the appended claims and the accompanying drawings in which:

FIG. 1 is a plan view of apparatus in accordance with a presently preferred embodiment of the invention;

FIG. 2 is a fragmentary sectional view of the measurement probe in the apparatus of FIG. 1, being taken substantially along the line 2—2 in FIG. 1;

FIG. 3 is a functional block diagram of the apparatus electronics;

DETAILED DESCRIPTION OF PREFERRED EMBODIMENTS

Figure 6:
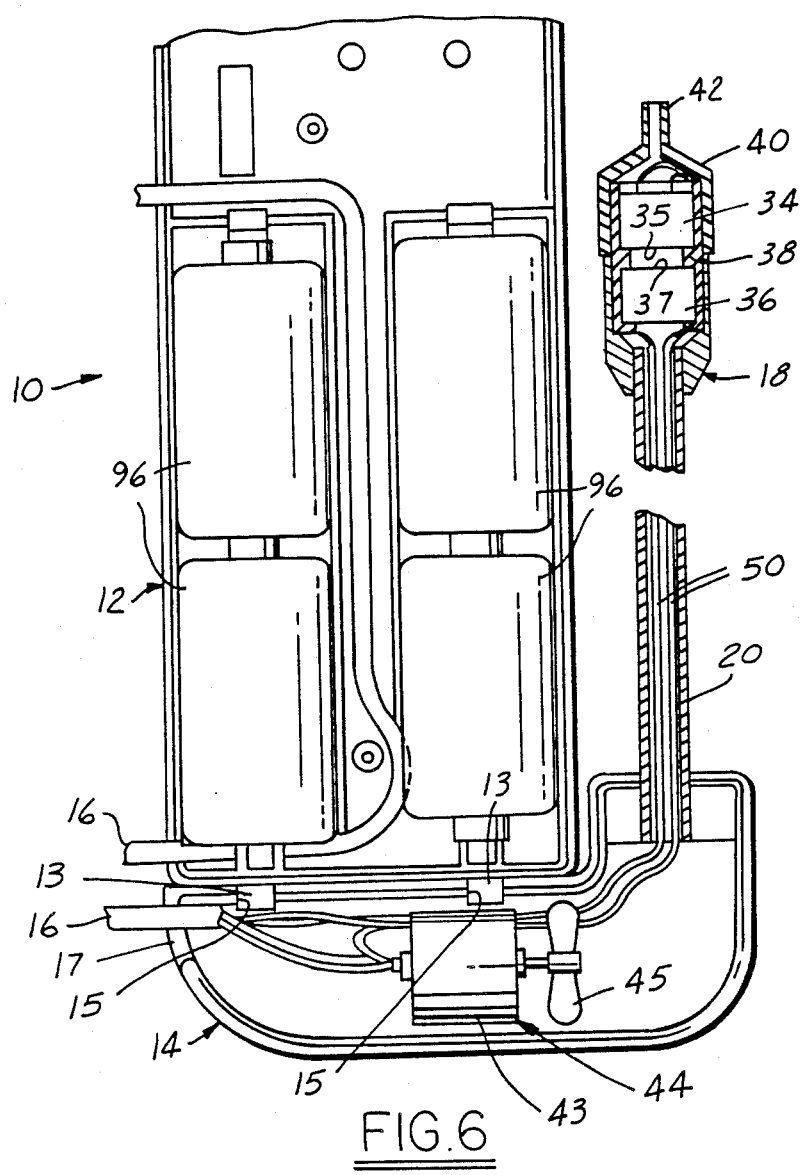
FIG. 6 is a fragmentary sectional view of a portion of the apparatus of FIG. 1 on an enlarged scale.

FIGS. 1 and 6 illustrate apparatus 10 in accordance with a presently preferred embodiment of the invention contained within an elongated housing 12 of molded plastic construction, for example. A hollow base 14 is removably mounted on housing 12 by means of tabs 13 (FIG. 6) which project from the lower edge of housing 12 being received by snap fit into opposing openings or apertures 15 in base 14. A motor 43 is mounted within base 14 and has an impeller 45 affixed thereto to form a fan 44. A sensor probe 18 is connected to base 14 by a hollow flexible conduit 20 and is removably seated within a socket 22 (FIG. 1) on enclosure 12 when base 14 is mounted thereto. Sensor probe 18 and fan 44 are coupled to electronics within housing 10 by a coiled multiple-conductor cord 16. A manual power/reset switch 24 is mounted for ready accessibility on a front panel 26 of enclosure 12 adjacent to a power LED 28 and an alarm LED 30. A grill 32 in panel 26 permits emission of audible contaminant alarm indications from the electronics contained within enclosure 12, as will be described hereafter. Apparatus 10 is powered by batteries 96 removably contained within housing 12.

Referring to FIGS. 2 and 6, sensor probe 18 includes a pair of ultrasonic transducers 34, 36, such as piezoelectric crystals, mounted in fixed positions spaced from each other within a protective cylindrical housing 38. Radiating surfaces 35, 37 of respective transducers 34, 36 are parallel to and spaced from each other within housing 38, spacing therebetween in the preferred embodiment of the invention being greater than one wavelength of ultrasonic energy at the preferred operating frequency (40KHz), but less than 1.5 wavelengths, when the sensor probe is operating in uncontaminated air. A probe tip 40 extends from one end of housing 38 and tapers to a narrow housing inlet 42. The opposing end of housing 38 is received within and communicates with conduit 20. Fan 44 (FIGS. 3, 4B and 6) positioned within base 14 draws test air through inlet 42, through internal grooves 46, 48 in housing 38, between transducer radiating surfaces 35, 37, and thence through conduit 20 which forms the probe outlet and a vent 17 in base 14 surrounding cord 16, whereby test air is continually drawn into and refreshed in the space between transducers 34, 36. Transducer leads 50 extend through conduit 20, base 14 and cord 16 to the apparatus electronics contained within housing 12. As best seen in FIG. 1, base 14 and the head 13 of enclosure 12 are of opposed generally L-shaped contour. Socket 22 on head 13 opens toward base 14. Probe 18 extends from the opposing side by base 14. Thus, with probe 18 received in socket 22 and base 14 on enclosure 12, the entire apparatus is of slim compact construction and may be readily carried in a toolbox or the like.

Figure 4A:
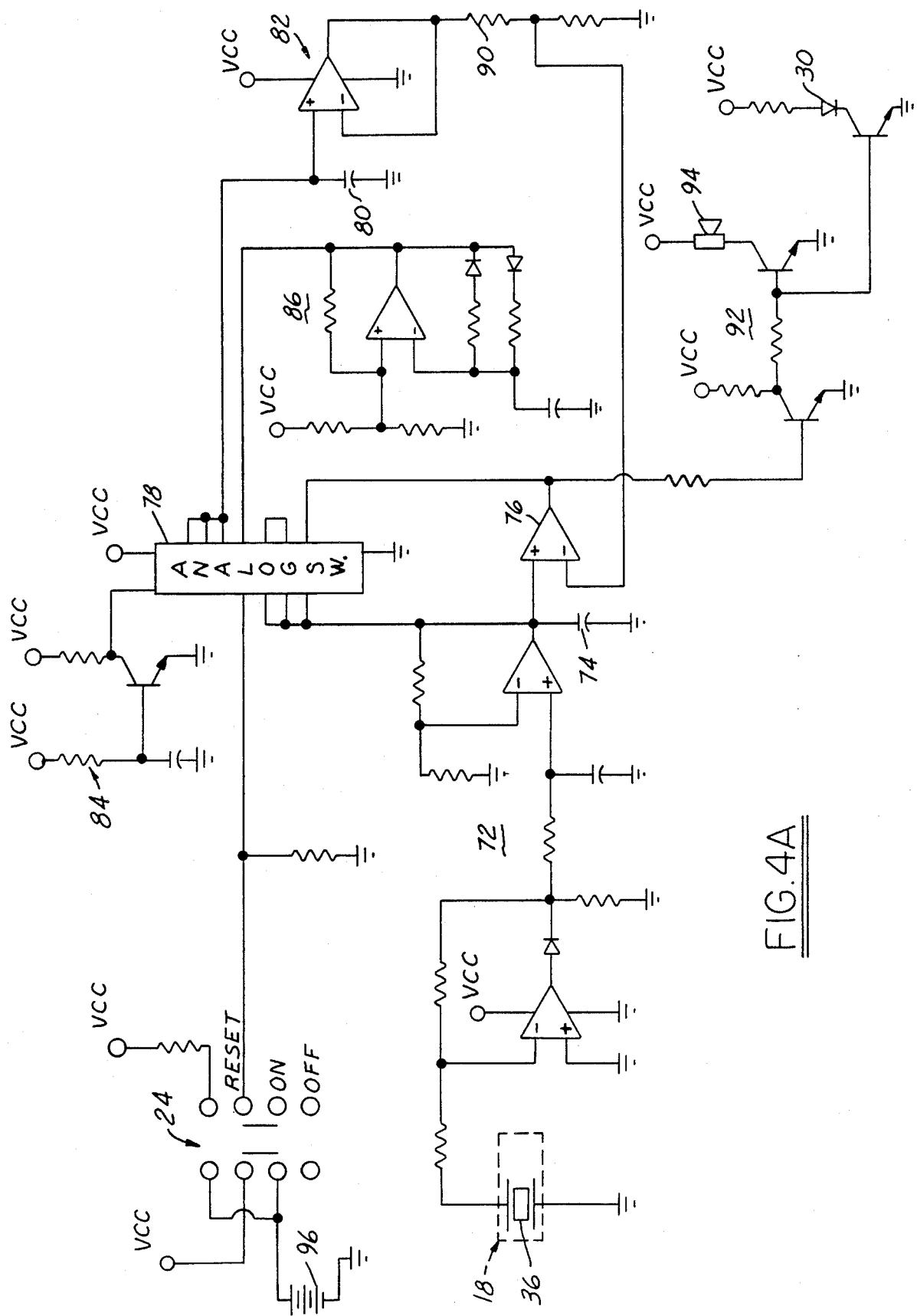
FIGS. 4A and 4B together comprise an electrical schematic diagram of the apparatus electronics illustrated in block form in FIG. 3.
Figure 4B:
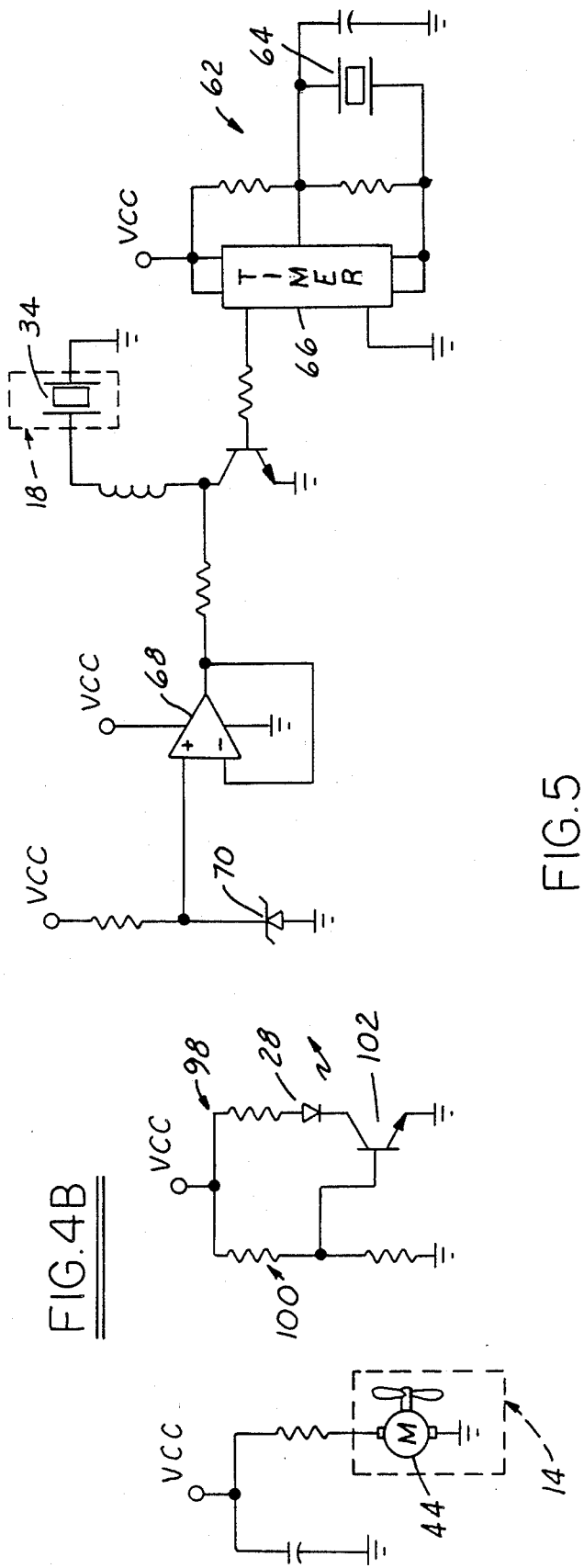

FIG. 3 is a functional block diagram of such apparatus electronics 60 in accordance with one embodiment of the invention, and FIGS. 4A and 4B illustrate the electronics in greater schematic detail. Transmitting crystal 34 is driven at constant frequency (40KHz) by an oscillator 62 (FIGS. 3 and 4B) which includes a crystal 64 coupled to a timer 66, and a voltage regulator 68 coupled to a zener diode 70. Receiving crystal 36 is connected to a full-wave precision rectifier 72 (FIGS. 3 and 4A) which provides across a capacitor 74 (FIG. 4A) a d.c. measurement output signal which varies as a function of peak-to-peak amplitude of energy received at transducer 36, which in turn varies with contaminant level as will be described. The measurement signal output of rectifier 72 is fed to the non-inverting input of a comparator 76, and also through the signal input and signal output of an analog switch 78 (FIGS. 3 and 4A) to the signal storage capacitor 80 (FIG. 4A) of a sample-and-hold amplifier 82. The control inputs of analog switch 78 are coupled to the RESET terminal of power/reset switch 24, to a circuit 84 responsive to initial application of power to the apparatus electronics, and to an oscillator 86 for generating a sampling pulse at preselected periodic intervals, such as every four seconds in the embodiment of FIGS. 3–4B (and every ½ second in the embodiment of FIGS. 7–8). Thus, the measurement signal appearing at the output of rectifier 72 is sampled and stored on capacitor 80 (FIG. 4A) of amplifier 82 when power is initially applied to the apparatus electronics, whenever the operator moves switch 24 to the RESET position, which preferably is a momentary contact switch position, and at preselected periodic intervals as controlled by oscillator 86.

A reference signal is derived from the measurement signal sampled and stored at capacitor 80 through a voltage divider 90 (FIG. 4A) coupled across the output of amplifier 82. The reference signal at the junction of divider 90 is applied to the inverting input of comparator 76. The output of comparator 76 is connected to an inhibit input of analog switch 78 for inhibiting automatic sampling of the measurement signal by oscillator 86 in the event of a contaminant alarm condition. The output of comparator 76 is also connected to an alarm circuit 92 which drives an audio alarm buzzer 94 (FIG. 4A) and contaminant alarm LED 30 (FIGS. 1 and 4A). Switch 24 in the preferred embodiment of the invention comprises a slide-type switch for applying power from batteries 96 contained within enclosure 12 (FIGS. 1 and 6) to a voltage bus Vcc in both the ON and RESET switch positions, and also for connecting the voltage bus to the manual reset control input of switch 78 in the RESET switch position. Fan 44 (FIGS. 3 and 4B) is continually powered in the ON and RESET positions of switch 24. A low-battery indicating circuit 98 (FIG. 4B) includes a voltage divider 100 and a transistor 102 for energizing power LED 28 when switch 24 is in the ON or RESET position as long as battery power remains above the threshold set by divider 100.

Figure 5:
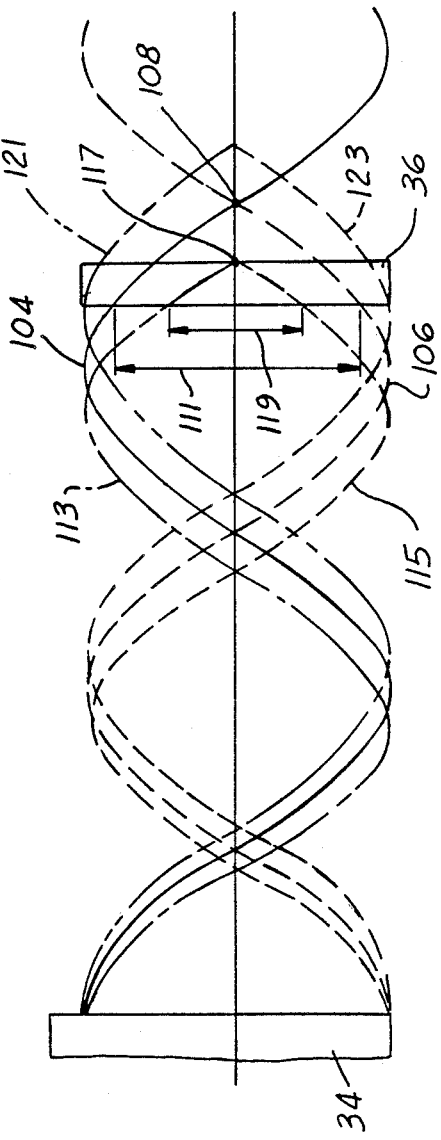
FIG. 5 is a graphic illustration useful in describing operation of the invention.

In operation, the apparatus of the present invention detects contaminant level, particularly halogen refrigerants, as a function of variation in velocity of ultrasonic radiation between transducer crystals 34, 36. Such velocity decreases in the presence of halogen agents as a continuous function of contaminant concentration. Since energization of transmitting crystals 34 is continuous and at constant frequency (as long as power is applied and ignoring long-term temperature effects, etc.), the wavelength of ultrasonic radiation between crystals 34, 36 thus varies with velocity and, hence, contaminant concentrations. Referring to FIG. 5, the curve 104 illustrates radiation from crystal 34 to crystal 36, and the curve 106 illustrates energy reflected by crystal 36 back to crystal 34 at design frequency and crystal spacing, and in the absence of contaminants. Curves 104, 106 thus exhibit a virtual node at point 108 behind crystal 36, and a peak-to-peak signal amplitude 111 at crystal 36, with a corresponding full-wave-rectified d.c. measurement signal at the output of rectifier 72 (FIGS. 3 and 4A). Such signal is sampled and stored at amplifier 82 to establish an ambient reference level.

If halogen concentration at probe 18 thereafter increases, velocity and wavelength of radiation between crystals 34, 36 decrease correspondingly to levels illustrated by curves 113, 115 (FIG. 5), for example. The virtual node 117 for these curves has moved to the left in FIG. 5, and the peak-to-peak signal amplitude 119 at crystal 36 has decreased correspondingly, yielding a correspondingly decreased measurement signal at the output of rectifier 72. When the measurement signal at the output of rectifier 72 decreases below the reference signal level, the output of comparator 76 switches to a low voltage stage, energizing audio/visual alarm 92, including buzzer 94 and LED 30. It will be be appreciated that the reference signal applied to the inverting input of comparator 76 is less than the previously-sampled measurement signal stored on capacitor 80 by virtue of unity gain characteristics of amplifier 82 and the voltage level reduction at voltage divider 90. This difference between the sampled measurement signal and the reference signal establishes a (negative) threshold, in effect, which the measurement signal must exceed to indicate an alarm condition. When such alarm condition is indicated, the low-voltage output of comparator 76 inhibits operation of switch 78 until the measurement signal at the output of rectifier 72 increases above the reference level, or until the reference level is manually reset through operator switch 24.

Figure 7:
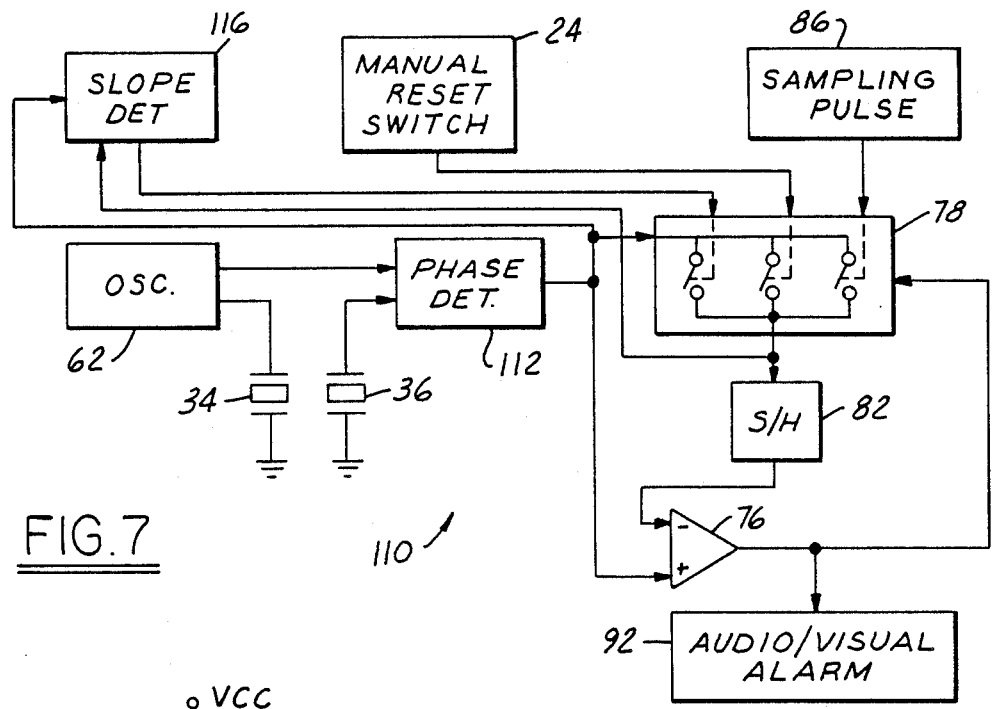
FIG. 7 is a functional block diagram of apparatus electronics in accordance with a modified embodiment of the invention.
Figure 8:
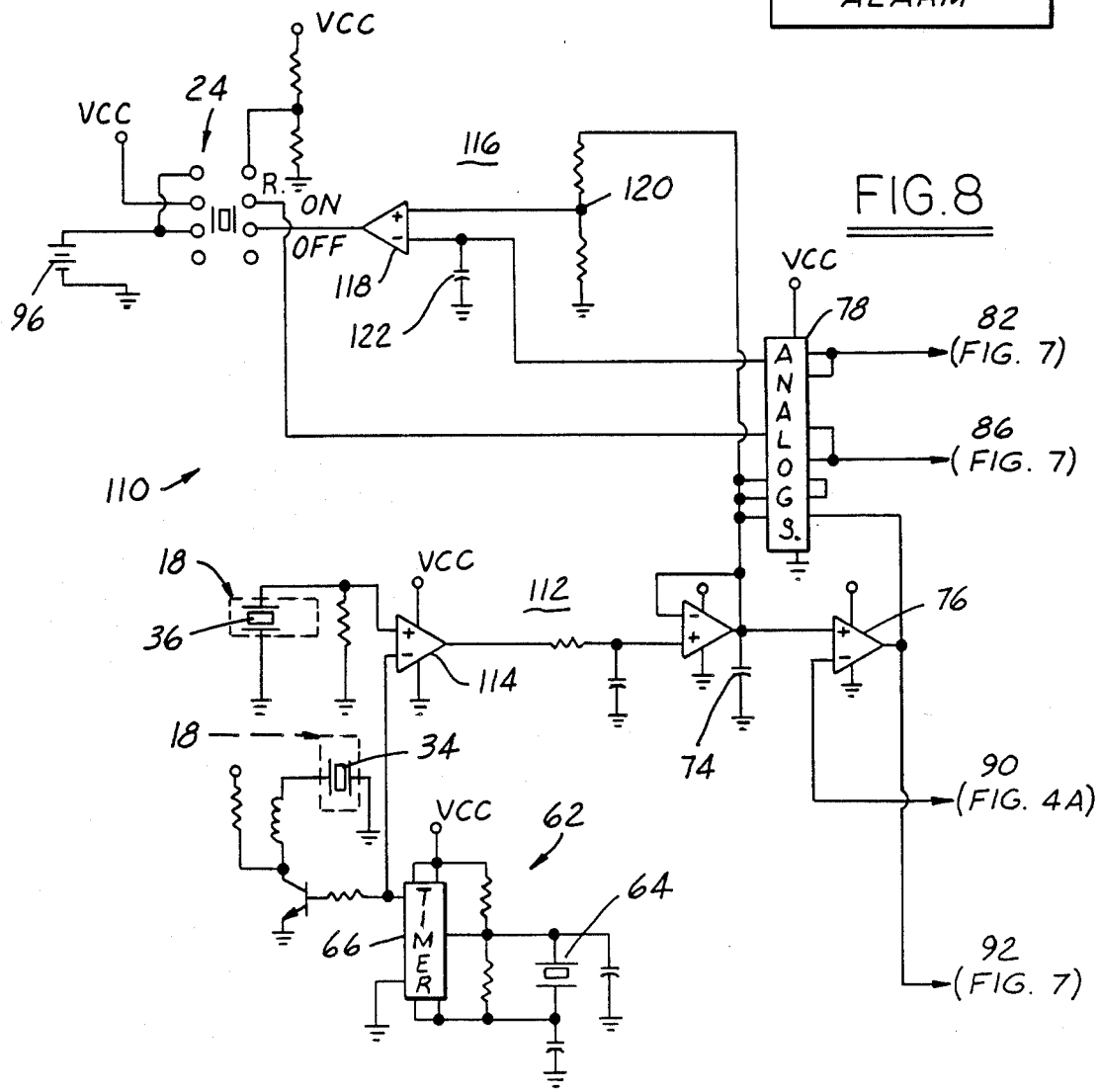
FIG. 8 is a fragmentary schematic diagram of the electronics of FIG. 7.

FIGS. 7 and 8 illustrate modified electronics 110 in accordance with a second embodiment of the invention. Portions of electronics 110 identical to portions of electronics 60 hereinabove described in detail are indicated by correspondingly identical reference numerals. In electronics 110, rectifier 72 in the embodiment of FIGS. 3-4B is replaced by a phase detector 112 which comprises a comparator 114 having its inverting input connected to the output of oscillator 62 and its non-inverting input connected to receiving crystal 36. Phase detector 112 thus provides across capacitor 74 a d.c. measurement output signal which varies as a function of phase differential between the oscillator output and energy received at crystal 36, which in turn varies with contaminant level. An advantage of the phase detection embodiment of FIGS. 7 and 8 is that circuit operation is substantially independent of temperature variations at probe 18 over the expected operating range, which may cause variations in separation between the radiating surfaces of crystals 34, 36.

Power-on reset circuit 84 (FIGS. 3 and 4A) is replaced in the embodiment of FIGS. 7 and 8 by a slope detector 116 which comprises a comparator 118 having its non-inverting input connected through a voltage divider 120 across capacitor 74 and its inverting input connected across a sample-and-hold capacitor 122 to an output of analog switch 78. The output of comparator 118 is connected through switch 24 in the ON position of the latter to a switch-controlling input of analog switch 78. When an alarm condition is detected, slope detector 116 functions to reset the alarm when contaminant level at probe 18 begins decreasing. When the measurement signal at capacitor 74 begins decreasing relative to the reference level at capacitor 122, the output of detector 116 operates switch 78 to set a new reference level at sample-and-hold circuit 82 (FIG. 7). The operator thus need not remove probe 18 from the contaminant area completely or otherwise wait until contaminant level decreases below the previous level at circuit 82. This feature enables more rapid location of a refrigerant leak. The remainder of electronics 110 is identical to that hereinabove described in conjunction with electronics 60.

A particular advantage in the embodiments of the invention hereinabove described is also illustrated in FIG. 5. That is, presence of moisture vapor in the test air increases rather than decreases velocity and wavelength of radiation, as illustrated by the transmission and reflection curves 121, 123 in FIG. 5. Such increase in velocity and wavelength is manifested by an increase rather than a decrease in both peak-to-peak amplitude and phase difference at crystal 36, and a correspondingly increased rather than decreased measurement signal level. Thus, such moisture vapor alone does not trip comparator 76 and energize alarms 94, 30. However, such moisture vapor will be taken into account at the next sampling pulse from oscillator 86, so that the waves 121, 123 will now represent the ambient reference level, and a decrease in wavelength (and velocity) to the curves 104, 106 may now indicate an alarm condition.

It will thus be appreciated that the apparatus 10 hereinabove described fully satisfies all of the objects and aims previously set forth. The apparatus may be hand-held, and probe tip 18 may be readily manipulated by virtue of flexible connecting conduit 20. Base 14 separable from enclosure 12 permits placement of the probe in hard-to-reach places. Moreover, the high-voltage tip of corona discharge leak-detector apparatus of the prior art has been entirely eliminated. The self-referencing feature of the present invention is particularly advantageous as compared with prior art ultrasonic gas analysis devices wherein a reference gas is contained in a separate tube. In this connection, it will be appreciated that the self-referencing feature of the invention not only eliminates necessity for changing the reference gas for differing environments, but in fact eliminates the reference gas tube entirely.

The invention claimed is:

1. Apparatus for detecting presence of contaminants in air comprising: sensor means including a spaced pair of radiant energy transducers, means for admitting a test air sample between said transducers, means for continuously applying a periodic signal to one of said transducers to launch radiant energy toward the other of said transducers, means including rectifier means coupled to said other of said transducers for providing an electrical measurement signal as a continuing d.c. output signal that is a function of velocity of radiant energy between said transducers, means for selectively sampling and electrically storing said measurement signal, means for deriving a reference signal from said sampled and stored measurement signal, means for continuously comparing said measurement signal to said reference signal, alarm means coupled to said continuous comparing means for indicating an alarm condition when a difference between said reference and measurement signals exceeds a preselected threshold indicating an increase in contaminants between said transducers, and means coupled to said continuously comparing means and to said alarm means and responsive to a change in said measurement signal indicating a decrease in contaminants following an indication of alarm condition at said alarm means for automatically resampling and storing said measurement signal as a new reference signal and thereby automatically terminating said indication of alarm condition at said alarm means.

2. The apparatus set forth in claim 1 wherein said means for providing said measurement signal comprises means responsive to phase angle between energies at said transducers; and wherein said signal-comparing means comprises means responsive to a decrease in measurement signal phase angle as compared with reference phase angle to indicate a said alarm condition, and being substantially independent of increase in said measurement signal phase angle and thereby independent of increase in humidity content between said transducers.

3. The apparatus set forth in claim 1 wherein said alarm means comprises audible alarm means, and means for energizing said audible alarm means when said measurement signal varies from said reference signal by more than said preselected threshold.

4. The apparatus set forth in claim 1 wherein said alarm means comprises illumination means, and means for energizing said illumination means in response to said alarm condition in the test air sample.

5. The apparatus set forth in claim 1 wherein said measurement signal is provided as a function of amplitude of energy received at the other of said transducers.

6. The apparatus set forth in claim 1 wherein said measurement signal is provided as a function of phase angle of energy received at the other of said transducers.

7. The apparatus set forth in claim 1 wherein said sensor means comprises a housing having said transducers mounted therewithin, means forming an air inlet and an air outlet in said housing, and fan means for drawing a test air sample through said inlet between said transducers and to said outlet.

8. The apparatus set forth in claim 1 wherein said sampling-and-storing means includes means for automatically sampling and storing said measurement signal at periodic intervals.

9. The apparatus set forth in claim 8 wherein said sampling-and-storing means includes operator switch means, and means responsive to actuation of said operator switch means for sampling and storing said measurement signal.

10. The apparatus set forth in claim 9 wherein said switch means comprises apparatus electrical power switch means, said actuation-responsive means being responsive to application of electrical power to said apparatus for automatically sampling and storing said measurement signal.

11. The apparatus set forth in claim 9
wherein said sampling-and-storing means comprises a sample-and-hold circuit including a capacitor for selectively storing said measurement signal, and analog switch means having a signal input coupled to said rectifier means, a signal output coupled to said sample-and-hold circuit, control inputs individually coupled to said switch means, to said means for automatically sampling at periodic intervals and to said decrease-responsive means, and an inhibit input coupled to said comparing means.

12. Apparatus for detecting contaminants in air comprising:
a sensor probe including a housing, a pair of ultrasonic transducers mounted within said housing at fixed positions spaced from each other, means forming an air inlet and an air outlet in said housing, a hollow base, a hollow flexible conduit connecting said housing outlet to said base, and a fan within said base for continuously drawing test air through said inlet, housing, conduit and base between said transducers, and
an elongated electronics enclosure including means for applying ultrasonic energy to one of said transducers and means responsive to energy received at the other of said transducers for determining contaminant level in said test air, means for removably affixing said base to said enclosure to form a unitary assembly, and means on said enclosure for indicating contaminant level to an operator.

13. Apparatus for detecting contaminants in air comprising:
a sensor probe including a housing, a pair of ultrasonic transducers mounted within said housing at fixed positions spaced from each other, means forming an air inlet and an air outlet in said housing, a hollow base, a hollow flexible conduit connecting said housing outlet to said base, and a fan within said base for continuously drawing test air through said inlet, housing, conduit and base between said transducers, and
an elongated electronics enclosure including means for applying ultrasonic energy to one of said transducers and means responsive to energy received at the other of said transducers for determining contaminant level in the test air, means for removably affixing said base to said enclosure to form a unitary assembly, and means on said enclosure for indicating contaminant level to an operator,
said base being of generally L-shaped construction and being removably affixed to said enclosure along one leg of said L-shaped construction with the other leg projecting along a side edge of said enclosure, said conduit and housing projecting from said other leg, said enclosure having an integral head of generally L-shaped construction opposed of said base, said head having a socket for removably receiving said housing inlet means when said base is affixed to said enclosure.

14. The apparatus set forth in claim 13 further comprising a multiple-conductor coiled cord connecting said electronics enclosure to said sensor probe.

15. The apparatus set forth in claim 14 wherein said electronics enclosure includes means for receiving batteries to power said apparatus.

16. The apparatus set forth in claim 15 wherein said electronics enclosure is constructed for holding lengthwise in an operator's hand.

17. coupled to said switch means, to said means for automatically sampling at periodical intervals and to said decrease-responsive means, and an inhibit input coupled to said comparing means.

18. Apparatus for detecting presence of contaminants in air comprising: sensor means including a spaced pair of radiant energy transducers, means for admitting a test air sample between said transducer, means for providing an electrical measurement signal as function of velocity of radiant energy between said transducers, means for selectively sampling and electrically storing said measurement signal, means for deriving a reference signal from a sampled and stored measurement signal, means for comparing said measurement signal to said reference signal and indicating an alarm condition when a difference between said reference and measurement signals exceeds a preselected threshold, and means responsive to a change in said measurement signal indicating a decrease in contaminants following an indication of an alarm condition for automatically resampling and storing said measurement signal as a new reference signal,
said means for providing said measurement signal comprising means responsive to phase angle between energies at said transducers; and said signal-comparing means comprising means responsive to a decrease in measurement signal phase angle as compared with reference phase angle to indicate a said alarm condition, and being substantially independent of increase in said measurement signal phase angle and thereby independent of increase in humidity content between said transducers.

19. Apparatus for detecting presence of halogen gas in air comprising:

sensor probe means including a housing having a central axis, a pair of ultrasonic transducers having identical nominal design frequencies mounted at fixed positions coaxially within said housing with radiating surfaces spaced from each other axially of said housing by a distance between 1.0 and 1.5 times ultrasonic wavelength at said nominal design frequency, means forming an air inlet and an air outlet at axially opposed ends of said housing coaxially with said housing, and means for continually drawing test air through said housing between said transducers, and an electronics package coupled to said probe and including means for applying ultrasonic energy to one of said transducers, and means responsive to ultrasonic energy received at the other of said transducers for indicating presence of halogen gas in air between said transducers, said energy-responsive means comprising means responsive to a decrease in ultrasonic energy at said other of said transducers for indicating presence of halogen gas, while being substantially independent of increase in energy at said other of said transducers and thereby being substantially independent of humidity between said transducers.

20. Apparatus for detecting presence of halogen gas in air comprising:

sensor probe means including a housing having a central axis, a pair of ultrasonic transducers having identical nominal design frequencies mounted at fixed positions coaxially within said housing with radiating surfaces spaced from each other axially of said housing by a distance between 1.0 and 1.5 times ultrasonic wavelength at said nominal design frequency, means forming an air inlet and an air outlet at axially opposed ends of said housing coaxially with said housing, and means for continually drawing test air through said housing between said transducers, and an electronics package coupled to said probe and including means for applying ultrasonic energy to one of said transducers, and means responsive to ultrasonic energy received at the other of said transducers for indicating presence of halogen gas in air between said transducers, said transducers being externally peripherally engaged by said housing, and said inlet and outlet means including a pair of diametrically opposed axially extending grooves in said housing adjacent and external to each said transducer periphery, a first of said pair of grooves being positioned ninety degrees around said housing with respect to the other said pair.

21. The apparatus set forth in claim 20 wherein said one of said transducers is positioned within said housing adjacent to said inlet, and wherein said inlet-forming means includes a conical tip that tapers narrowingly from said housing to said inlet and is spaced from said one transducer to permit passage of that air therebetween.

22. Apparatus for detecting presence of halogen gas in air comprising:

sensor probe means including a housing having a central axis, a pair of ultrasonic transducers having identical nominal design frequencies mounted at fixed positions coaxially within said housing with radiating surfaces spaced from each other axially of said housing by a distance between 1.0 and 1.5 times ultrasonic wavelength at said nominal design frequency, means forming an air inlet and an air outlet at axially opposed ends of said housing coaxially with said housing, and means for continually drawing test air through said housing between said transducers, and an electronics package coupled to said probe and including means for applying ultrasonic energy to one of said transducers, and means responsive to ultrasonic energy received at the other of said transducers for indicating presence of halogen gas in air between said transducers, the entire said apparatus comprising an elongated enclosure contoured for holding in an operator's hand, said sensor probe means comprising a base removably affixed to said enclosure, a fan within said base and a hollow flexible conduit connecting said base to said housing, test air being drawn by said fan through said probe housing, said conduit and thence into and discharged from said base, the remainder of said apparatus being contained within said enclosure and being connected to said sensor probe means by a multiple-conductor coiled cord.

* * * * *